United States Patent
Makeev

(10) Patent No.: US 7,312,035 B2
(45) Date of Patent: Dec. 25, 2007

(54) METHODS OF GENETIC ANALYSIS OF YEAST

(75) Inventor: Tanya Makeev, Cupertino, CA (US)

(73) Assignee: Affymetrix, Inc., Santa Clara, CA (US)

( * ) Notice: Subject to any disclaimer, the term of this patent is extended or adjusted under 35 U.S.C. 154(b) by 413 days.

(21) Appl. No.: 10/934,048

(22) Filed: Sep. 3, 2004

(65) Prior Publication Data

US 2006/0051770 A1    Mar. 9, 2006

(51) Int. Cl.
  C12M 1/34   (2006.01)
  C12M 3/00   (2006.01)
  C07H 21/04  (2006.01)
  C12Q 1/68   (2006.01)

(52) U.S. Cl. ............ 435/6; 435/91.1; 435/287.2; 536/23.1; 536/24.3

(58) Field of Classification Search ............ None
  See application file for complete search history.

(56) References Cited

U.S. PATENT DOCUMENTS

| | | | |
|---|---|---|---|
| 5,143,854 | A | 9/1992 | Pirrung et al. |
| 5,800,992 | A | 9/1998 | Fodor et al. |
| 5,994,075 | A | 11/1999 | Goodfellow |
| 6,309,822 | B1 * | 10/2001 | Fodor et al. ............ 435/6 |
| 6,821,724 | B1 | 11/2004 | Mittman et al. |
| 2003/0044866 | A1 | 3/2003 | Boone |

OTHER PUBLICATIONS

Affymetrix GeneChip Yeast Genome 2.0 array (2004-2005).*
Genbank Accession Nos. NC_001133-NC_001148, and NC_001224.*
(Wood et al; Nature, vol. 412, 2002, pp. 871-880.*
Chen et al; Molecular Biology of the Cell, Jan. 2003, vol. 14, pp. 214-229.*
Lashkari et al; PNAS, vol. 94, pp. 13057-13062; 1997.*
Wodicka et al, Genome-wide expression monitoring in *Saccharomyces cerevisiae*, Nature Biotechnology 15:1359-1367 (1997).
Affymetrix GeneChip Ye6100 Instructions for use, PN 700163 Rev. 1, May 1998.
GeneChip Yeast Genome S98 array Product Insert, PN 700290 Rev. 1, Feb. 2000.
Winzeler et al., Direct allelic variation scanning of the yeast genome, Science 281:1194-7 (1998).
Lockhart et al., Expression monitoring by hybridization to high-density oligonucleotide arrays, Nat. Biotech 14:1675-80 (1996).
Lashkari et al., Yeast microarrays for genome wide parallel genetic and gene expression analysis, PNAS 94:13057-62 (1997).
Talla et al., A novel design of whole-genome microarray probes for *Saccharomyces cerevisiae* which minimizes cross hybridization, BMC Genomic 4:38 (2003).
Bosch et al., Operon Array-Ready Oligo Sets provide sequence-optimized 70mers for DNA microarrays, QiagenNews 4:1, 10-11 (2001).
Frey et al., Gene Expression Arrays: Highly sensitive detection of expression patterns with improved tools for target amplification, Biochemica 2:27-29 (2002).
Bernstein et al., Methylation of histone H3 Lys 4 in coding regions of active genes, PNAS 99:8695-8700 (2002).

* cited by examiner

*Primary Examiner*—Jehanne Sitton
(74) *Attorney, Agent, or Firm*—Sandra E. Wells

(57) ABSTRACT

Arrays of oligonucleotide probes which are complementary to a plurality of *S. cerevisisae* and *S. pombe* genes are disclosed. The arrays may be used to measure the expression levels of a plurality of genes simultaneously.

15 Claims, No Drawings

METHODS OF GENETIC ANALYSIS OF YEAST

FIELD OF THE INVENTION

Arrays of oligonucleotide probes complementary to selected genomic regions of yeast are disclosed. The arrays may be used to monitor the expression of a plurality of genes in parallel. The invention therefore relates to diverse fields impacted by the nature of molecular interaction, including chemistry, biology, medicine, and medical diagnostics.

REFERENCE TO SEQUENCE LISTING

The Sequence Listing submitted on compact disk is hereby incorporated by reference. The file on the disk is named 3699seqlist.txt, the file is 17,106 KB and the date of creation is Sep. 2, 2004.

BACKGROUND OF THE INVENTION

Many biological functions are carried out by regulating the expression levels of various genes, either through changes in levels of transcription (e.g. through control of initiation, provision of RNA precursors, RNA processing, etc.) of particular genes, through changes in the copy number of the genetic DNA, through changes in RNA processing such as polyadenylation and splicing or RNA stability or through changes in protein synthesis. For example, control of the cell cycle and cell differentiation, as well as diseases, are characterized by the variations in the transcription levels of a group of genes. Gene expression is not only responsible for physiological functions, but also associated with pathogenesis. For example, the lack of sufficient functional tumor suppressor genes and/or the over expression of oncogene/protooncogenes leads to tumorgenesis. (See, e.g., Marshall, Cell, 64: 313-326 (1991) and Weinberg, Science, 254: 1138-1146 (1991)). Thus, changes in the expression levels of particular genes (e.g. oncogenes or tumor suppressors), serve as signposts for the presence and progression of various diseases.

Arrays of probes to the yeast *Saccharomyces cerevisisae* have been available, for example, the Affymetrix Yeast Genome S98 array, described in U.S. patent application Ser. No. 09/953,570 and the Ye6100 array set. Probe selection for each of these arrays was based on the *S. cerevisiae* genome sequence information available at the time of the array design. Over time the public databases of genomic sequence are updated and refined to reflect new information. As such, our understanding of the genome changes over time, for example, sequencing errors are corrected, polymorphisms are identified, transcripts are mapped more accurately, new genes are identified, exon-intron boundaries are mapped, and transcription start sites and polyadenylation sites are mapped. Arrays useful for monitoring expression need to change to reflect changes in the genomic sequence and annotations to the genome.

SUMMARY OF THE INVENTION

Arrays of oligonucleotide probes for monitoring the expression of yeast genes are disclosed. In a preferred embodiment an array comprising nucleic acid probes where each probe is one of the sequences listed in SEQ ID Nos. 1-120,855 is disclosed. Each probe sequence may be present in a feature of known or determinable location that can be distinguished from other features that contain probes of different sequence. In one embodiment each different probe sequence is present in a different area on the surface of a solid support.

In one embodiment the invention comprises an array comprising any 10 or more, 100 or more, 1000, or more, 10,000 or more or 100,000 or more nucleic acid probes containing 15 or more consecutive nucleotides from the sequences listed in SEQ ID NOS: 1-120,855, or the complement thereof. In a further embodiment, the invention comprises the use of any of the disclosed arrays to: monitor gene expression levels by hybridization of the array to a nucleic acid library; monitor gene expression levels by hybridization to an mRNA-protein fusion compound; identify polymorphisms; identify biallelic markers; produce genetic maps; analyze genetic variation; comparatively analyze gene expression between different species, different strains or samples that have undergone different treatments, or to analyze gene knockouts. In a further embodiment the invention comprises a method of analysis comprising hybridizing one or more pools of nucleic acids to an array comprising at least 1,000 or more of the probes disclosed in SEQ ID Nos. 1-120,855 and detecting said hybridization. In a further embodiment the invention comprises the use of any one or more of the fragments disclosed in SEQ ID Nos. 1-120,855 as a primer for PCR. In a further embodiment the invention comprises the use of any one or more of the fragments disclosed in SEQ ID Nos. 1-120,855 as a ligand. In another embodiment each of the sequences in SEQ ID Nos. 1-120, 855 is synthesized on an array as a probe and the array is used to monitor gene expression from a biological sample isolated from yeast.

DETAILED DESCRIPTION OF THE INVENTION

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (*Vols. I-IV*), *Using Antibodies: A Laboratory Manual, Cells: A Laboratory Manual, PCR Primer: A Laboratory Manual*, and Molecular *Cloning: A Laboratory Manual* (all from Cold Spring Harbor Laboratory Press), Stryer, L. (1995) *Biochemistry* (4th Ed.) Freeman, New York, Gait, *"Oligonucleotide Synthesis: A Practical Approach"* 1984, IRL Press, London, Nelson and Cox (2000), *Lehninger, Principles of Biochemistry* $3^{rd}$ Ed., W.H. Freeman Pub., New York, N.Y. and Berg et al. (2002) *Biochemistry*, $5^{th}$ Ed., W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication No. WO 99/36760) and PCT/US01/04285 (International Publication No. WO 01/58593), which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 10/442,021, 10/013,598 (U.S. Patent Application Publication 20030036069), and U.S. Pat. Nos. 5,856,092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506.

The present invention also contemplates sample preparation methods in certain preferred embodiments. Prior to or concurrent with genotyping, the genomic sample may be amplified by a variety of mechanisms, some of which may employ PCR. See, for example, *PCR Technology: Principles and Applications for DNA Amplification* (Ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); PCR (Eds. McPherson et al., IRL Press, Oxford); and U.S. Pat. Nos. 4,683,202, 4,683,195, 4,800,159 4,965,188, and 5,333,675, and each of which is incorporated herein by reference in their entireties for all purposes. The sample may be amplified on the array. See, for example, U.S. Pat. No. 6,300,070 and U.S. Ser. No. 09/513,300, which are incorporated herein by reference.

Other suitable amplification methods include the ligase chain reaction (LCR) (for example, Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA*, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517, and 6,063,603, each of which is incorporated herein by reference). Other amplification methods that may be used are described in, U.S. Pat. Nos. 5,242,794, 5,494,810, 4,988,617 and in U.S. Ser. No. 09/854,317, each of which is incorporated herein by reference.

Additional methods of sample preparation and techniques for reducing the complexity of a nucleic sample are described in Dong et al., *Genome Research* 11, 1418 (2001), in U.S. Pat. Nos. 6,361,947, 6,391,592 and U.S. Ser. Nos. 09/916,135, 09/920,491 (U.S. Patent Application Publication 20030096235), Ser. No. 09/910,292 (U.S. Patent Application Publication 20030082543), and Ser. No. 10/013,598.

Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* ($2^{nd}$ Ed. Cold Spring Harbor, N.Y, 1989); Berger and Kimmel *Methods in Enzymology*, Vol. 152, *Guide to Molecular Cloning Techniques* (Academic Press, Inc., San Diego, Calif., 1987); Young and Davism, *P.N.A.S*, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference The present invention also contemplates signal detection of hybridization between ligands in certain preferred embodiments. For example, methods and apparatus for signal detection and processing of intensity data are disclosed in, U.S. Pat. Nos. 5,143,854; 5,547,839; 5,578,832; 5,631,734; 5,800,992; 5,834,758; 5,856,092; 5,902,723; 5,936,324; 5,981,956; 6,025,601; 6,090,555; 6,141,096; 6,171,793; 6,185,030; 6,201,639; 6,207,960; 6,218,803; 6,225,625; 6,252,236; 6,335,824; 6,403,320; 6,407,858; 6,472,671; 6,490,533; 6,650,411; and 6,643,015, in U.S. patent application Ser. No. 10/389,194, 60/493,495 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis Bioinformatics: A Practical Guide for Analysis of Gene and Proteins (Wiley & Sons, Inc., 2nd ed., 2001). See U.S. Pat. No. 6,420,108.

The present invention may also make use of various computer program products and software for a variety of purposes, such as probe design, management of data, analysis, and instrument operation. See, U.S. Pat. Nos. 5,733,729; 5,593,839; 5,795,716; 5,733,729; 5,974,164; 6,066,454; 6,090,555; 6,185,561; 6,188,783; 6,223,127; 6,228,593; 6,229,911; 6,242,180; 6,308,170; 6,361,937; 6,420,108; 6,484,183; 6,505,125; 6,510,391; 6,532,462; 6,546,340; and 6,687,692.

Additionally, the present invention may have preferred embodiments that include methods for providing genetic information over networks such as the Internet as shown in U.S. Ser. Nos. 10/197,621, 10/063,559 (United States Publication Number 20020183936), Ser. Nos. 10/065,856, 10/065,868, 10/328,818, 10/328,872, 10/423,403, and 60/482,389.

I. Definitions

The term "array" as used herein refers to an intentionally created collection of molecules which can be prepared either synthetically or biosynthetically. The molecules in the array can be identical or different from each other. The array can assume a variety of formats, for example, libraries of soluble molecules; libraries of compounds tethered to resin beads, silica chips, or other solid supports.

The term "combinatorial synthesis strategy" as used herein refers to a combinatorial synthesis strategy is an ordered strategy for parallel synthesis of diverse polymer sequences by sequential addition of reagents which may be represented by a reactant matrix and a switch matrix, the product of which is a product matrix. A reactant matrix is a 1 column by m row matrix of the building blocks to be added. The switch matrix is all or a subset of the binary numbers, preferably ordered, between 1 and m arranged in columns. A "binary strategy" is one in which at least two successive steps illuminate a portion, often half, of a region of interest on the substrate. In a binary synthesis strategy, all possible compounds which can be formed from an ordered set of reactants are formed. In most preferred embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme. A combinatorial "masking" strategy is a synthesis which uses light or other spatially selective deprotecting or activating agents to remove protecting groups from materials for addition of other materials such as amino acids.

The term "complementary" as used herein refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

The term "genome" as used herein is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

The term "hybridization" as used herein refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." Hybridizations are usually performed under stringent conditions, for example, at a salt concentration of no more than about 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations or conditions of 100 mM MES, 1 M [Na$^+$], 20 mM EDTA, 0.01% Tween-20 and a temperature of 30-50° C., preferably at about 45-50° C. Hybridizations may be performed in the presence of agents such as herring sperm DNA at about 0.1 mg/ml, acetylated BSA at about 0.5 mg/ml. As other factors may affect the stringency of hybridization, including base composition and length of the complementary strands, presence of organic solvents and extent of base mismatching, the combination of parameters is more important than the absolute measure of any one alone. Hybridization conditions suitable for microarrays are described in the Gene Expression Technical Manual, 2004 and the GeneChip Mapping Assay Manual, 2004.

The term "hybridization probes" as used herein are oligonucleotides capable of binding in a base-specific manner to a complementary strand of nucleic acid. Such probes include peptide nucleic acids, as described in Nielsen et al., *Science* 254, 1497-1500 (1991), LNAs, as described in Koshkin et al. *Tetrahedron* 54:3607-3630, 1998, and U.S. Pat. No. 6,268,490, aptamers, and other nucleic acid analogs and nucleic acid mimetics.

The term "hybridizing specifically to" as used herein refers to the binding, duplexing, or hybridizing of a molecule only to a particular nucleotide sequence or sequences under stringent conditions when that sequence is present in a complex mixture (for example, total cellular) DNA or RNA.

The term "initiation biomonomer" or "initiator biomonomer" as used herein is meant to indicate the first biomonomer which is covalently attached via reactive nucleophiles to the surface of the polymer, or the first biomonomer which is attached to a linker or spacer arm attached to the polymer, the linker or spacer arm being attached to the polymer via reactive nucleophiles.

The term "isolated nucleic acid" as used herein mean an object species invention that is the predominant species present (i.e., on a molar basis it is more abundant than any other individual species in the composition). Preferably, an isolated nucleic acid comprises at least about 50, 80 or 90% (on a molar basis) of all macromolecular species present. Most preferably, the object species is purified to essential homogeneity (contaminant species cannot be detected in the composition by conventional detection methods).

The term "ligand" as used herein refers to a molecule that is recognized by a particular receptor. The agent bound by or reacting with a receptor is called a "ligand," a term which is definitionally meaningful only in terms of its counterpart receptor. The term "ligand" does not imply any particular molecular size or other structural or compositional feature other than that the substance in question is capable of binding or otherwise interacting with the receptor. Also, a ligand may serve either as the natural ligand to which the receptor binds, or as a functional analogue that may act as an agonist or antagonist. Examples of ligands that can be investigated by this invention include, but are not restricted to, agonists and antagonists for cell membrane receptors, toxins and venoms, viral epitopes, hormones (for example, opiates, steroids, etc.), hormone receptors, peptides, enzymes, enzyme substrates, substrate analogs, transition state analogs, cofactors, drugs, proteins, and antibodies.

The phrase "massively parallel screening" refers to the simultaneous screening of at least about 100, about 1000, about 10,000, about 100,000 or about 500,000 different nucleic acid hybridizations, preferably in a single reaction or experiment.

Mismatch: The term "mismatch," "mismatch control" or "mismatch probe" refers to a nucleic acid whose sequence is deliberately designed not to be perfectly complementary to a particular target sequence. As a non-limiting example, for each mismatch (MM) control in a high-density probe array there typically exists a corresponding perfect match (PM) probe that is perfectly complementary to the same particular target sequence. The mismatch may comprise one or more bases. While the mismatch(es) may be located anywhere in the mismatch probe, terminal mismatches are less desirable because a terminal mismatch is less likely to prevent hybridization of the target sequence. In a particularly preferred embodiment, the mismatch is located at the center of the probe, for example if the probe is 25 bases the mismatch position is position 13, also termed the central position, such that the mismatch is most likely to destabilize the duplex with the target sequence under the test hybridization conditions. A homo-mismatch substitutes an adenine (A) for a thymine (T) and vice versa and a guanine (G) for a cytosine (C) and vice versa. For example, if the target sequence was: 5'-AGGTCCA-3', a probe designed with a single homo-mismatch at the central, or fourth position, would result in the following sequence: 3'-TCCTGGT-5', the PM probe would be 3'-TCCAGGT-5'.

The term "mixed population" or sometimes refer by "complex population" as used herein refers to any sample containing both desired and undesired nucleic acids. As a non-limiting example, a complex population of nucleic acids may be total genomic DNA, total genomic RNA or a combination thereof. Moreover, a complex population of nucleic acids may have been enriched for a given population but may include other undesirable populations. For example, a complex population of nucleic acids may be a sample which has been enriched for desired messenger RNA (mRNA) sequences but still includes some undesired ribosomal RNA sequences (rRNA).

The term "monomer" as used herein refers to any member of the set of molecules that can be joined together to form an oligomer or polymer. The set of monomers useful in the present invention includes, but is not restricted to, for the example of (poly)peptide synthesis, the set of L-amino acids, D-amino acids, or synthetic amino acids. As used herein, "monomer" refers to any member of a basis set for synthesis of an oligomer. For example, dimers of L-amino acids form a basis set of 400 "monomers" for synthesis of polypeptides. Different basis sets of monomers may be used at successive steps in the synthesis of a polymer. The term "monomer" also refers to a chemical subunit that can be combined with a different chemical subunit to form a compound larger than either subunit alone.

The term "mRNA" or sometimes refer by "mRNA transcripts" as used herein, include, but not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

The term "nucleic acid library" or sometimes refer by "array" as used herein refers to an intentionally created collection of nucleic acids which can be prepared either synthetically or biosynthetically and screened for biological activity in a variety of different formats (for example, libraries of soluble molecules; and libraries of oligos tethered to resin beads, silica chips, or other solid supports). Additionally, the term "array" is meant to include those libraries of nucleic acids which can be prepared by spotting nucleic acids of essentially any length (for example, from 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

The term "nucleic acids" as used herein may include any polymer or oligomer of pyrimidine and purine bases, preferably cytosine, thymine, and uracil, and adenine and guanine, respectively. See Albert L. Lehninger, PRINCIPLES OF BIOCHEMISTRY, at 793-800 (Worth Pub. 1982). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

The term "oligonucleotide" or sometimes refer by "polynucleotide" as used herein refers to a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof. A further example of a polynucleotide of the present invention may be peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

Perfect match: The term "match," "perfect match," "perfect match probe" or "perfect match control" refers to a nucleic acid that has a sequence that is designed to be perfectly complementary to a particular target sequence or portion thereof. For example, if the target sequence is 5'-GATTGCATA-3' the perfect complement is 5'-TATGCAATC-3'. Where the target sequence is longer than the probe the probe is typically perfectly complementary to a portion (subsequence) of the target sequence. For example, if the target sequence is a fragment that is 800 bases, the perfect match probe may be perfectly complementary to a 25 base region of the target. A perfect match (PM) probe can be a "test probe", a "normalization control" probe, an expression level control probe and the like. A perfect match control or perfect match is, however, distinguished from a "mismatch" or "mismatch probe."

The term "primer" as used herein refers to a single-stranded oligonucleotide capable of acting as a point of initiation for template-directed DNA synthesis under suitable conditions for example, buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

The term "probe" as used herein refers to a surface-immobilized molecule that can be recognized by a particular target. See U.S. Pat. No. 6,582,908 for an example of arrays having all possible combinations of probes with 10, 12, and more bases. Examples of probes that can be investigated by this invention include, but are not restricted to, agonists and antagonists for cell membrane receptors, toxins and venoms, viral epitopes, hormones (for example, opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

The term "solid support", "support", and "substrate" as used herein are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates.

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as anti-probes. As the term targets is used herein, no difference in meaning is intended. A "Probe Target Pair" is formed when two macromolecules have combined through molecular recognition to form a complex.

II. Yeast Array

Although yeast is unicellular, it is an ideal model organism for studying eukaryotic cellular and disease processes. The shorter cell cycle of the yeast compared to higher eukaryotes makes it easier to observe cell processes, study biochemical functions and screen compounds. In one embodiment an array is disclosed that allows for simultaneous measurement of relative gene expression levels for a plurality of yeast genes from Saccharomyces cerevisiae, budding yeast, and Schizosaccharomyces pombe, fission yeast. S. cerevisiae is an important model organism for comparative genomics studies to model biochemical and genetic pathways because of the high degree of homology with the human genome. S. cerevisiae is also an important organism for identifying pathways required for fungal survival in a mammalian host environment and for studying phenotypic variation and instability. S. pombe is a fundamental model organism for studying differential gene regulation, cell-cycle control, signal transduction, cellular morphogenesis, and genome organization. Many genes found in S. pombe and S. cerevisiae are highly homologous to human genes known to be involved in human diseases, including many that are relevant to cancer genetics. Gene expression monitoring may also be used to optimize culture conditions to improve yields of recombinant proteins in metabolite production.

In a preferred embodiment an array comprising a plurality of probe sets for detection of expression products from S. cerevisiae, a plurality of probe sets for detection of expression products from S. pombe and a plurality of control probes are disclosed. In a preferred embodiment an array is disclosed that comprises each of the sequences listed in the sequence listing attached to a solid support in a different determinable location. Each sequence in the sequence listing is present in a location, or feature, that is preferably distinct or distinguishable from each of the other sequences in the sequence listing, features may overlap to some extent. A probe set may comprise a plurality of different oligonucleotide probes that are complementary to the same transcript but to different regions of the transcript. Each probe in the probe set may be present in a unique feature. In a preferred embodiment a probe set is comprised of probe pairs and a probe pair is a perfect match probe and the corresponding mismatch probe. The mismatch probe is identical to the perfect match probe except for a mismatch at the central position, position 13 of a 25 mer probe. Mismatch probes may be included on the array for use as controls to measure discrimination and specificity. Antisense probes that are derived from the opposite strand of the gene may also be included.

In preferred embodiments the array comprises a plurality of control probes. Control probes may include, for example, hybridization controls, poly-A controls, manufacturing controls and housekeeping control genes. Hybridization controls may be from an organism other than the organism being studies. In a preferred embodiment probes for the E. coli bioB, bioC, and bioD genes and probes for the P1 Bacteriophage cre gene are included as hybridization controls. A mixture of the transcripts that are complementary to the probe may be included in the hybridization. Probes for B. subtilis dap, lys, phe, thr, and trp genes may be included and used for sample preparation controls. Normalization controls may include probes for GAPDH, Actin, EAf5, SRB4, tfIId, RIP1, URA3 and WBP1. Ribosomal RNA probes may also be included. Other control sequence probes may also be included. Control probes may be included to assay for manufacturing defects, problems with sample preparation and problems with hybridization. Probes for synthetic sequences that are not present in the genome being assayed and are preferably not present in other known genomes may also be included, for example, tag probes such as those disclosed in U.S. patent application Ser. No. 09/827,383.

In a preferred embodiment the array is a single solid support so that the expression levels for at least 5,000 S. cerevisiae transcripts and at least 5,000 S. pombe transcripts may be simultaneously analyzed in a single experiment using a single hybridization. See, for example the U133 Plus 2.0 Array available from Affymetrix. This array allows analysis of over 47,000 human transcripts on a single chip. In another embodiment the probes are divided so that they are on two or more chips or solid supports. Arrays may also be attached to pegs for high throughput analysis. In a preferred embodiment a plurality of the disclosed arrays are attached to pegs in a format that allows hybridization of the arrays in 96 or 384 well microtitre dish format, facilitating highly parallel analysis of a plurality of different samples. In a preferred embodiment sample preparation and array hybridization, staining and washing are performed in an automated manner.

The genomes of S. cerevisisae and S. pombe have been sequenced and are publicly available. The disclosed probe sequences were designed using information from GenBank (May 2004) for S. cerevisisae and from the Sanger Center (June 2004) for S. pombe. The disclosed arrays represent an improvement over arrays present in the prior art because our understanding of the yeast genome has improved. The probes disclosed in the sequence listing were selected using computer based methods such as those described in U.S. Pat. No. 6,309,822. Probe sets typically include 11 oligonucleotide probe pairs. For most probe sets all of the probes in the set are designed to detect the same transcript.

When measuring expression one of skill in the art will recognize that the probes of the array should be designed to be complementary to the sequence to be detected. This may vary depending on which amplification method is used. For example, one method of amplification calls for reverse transcription of the mRNA using an oligo-dt-T7 primer. Double stranded cDNA with an RNA polymerase promoter is then generated and antisense RNA is transcribed and labeled. The antisense RNA is then hybridized to the array. The antisense RNA is complementary to the mRNA so the probes on the array should hybridize to the antisense RNA and should be identical in sequence to a portion of the transcribed mRNA. In another method the amplified nucleic acid to be hybridized to the array is sense, meaning that it has the same sequence as the starting mRNA so the probes should be complementary to the transcribed mRNA. In other embodiments the amplification product that is hybridized to the array may be cDNA that may be in the sense (same as) or antisense (complement of) orientation relative to the starting mRNA.

The present invention provides a pool of unique nucleotide sequences complementary to yeast sequences in particular embodiments which alone, or in combinations of 2 or more, 10 or more, 100 or more, 1,000 or more, 10,000 or more, or 100,000 or more, can be used for a variety of applications.

In one embodiment a high density array of probes suitable for array based massive parallel gene expression of two species of yeast is disclosed. Array based methods for monitoring gene expression are disclosed and discussed in detail in U.S. Pat. No. 5,800,992, U.S. Pat. No. 6,309,822, and PCT Application WO 92/10588 (published on Jun. 25, 1992). Methods of monitoring gene expression are well known. The probes may be arranged into different localized areas, or features, that are about 5 to about 24 square microns in size. Each feature may have many copies of the same probe sequence, for example, more than 1,000, 10,000, 100,000 or 1,000,000 copies of the same sequence. Within a feature some truncated versions of the probe sequence may be present. The borders of individual features may or may not overlap with other features. In another embodiment each different probe sequence is present on a bead. The identity of the probe sequence on the bead may be determined by marking each probe sequence or each bead with a detectable marker or label, for example, a tag sequence. A decoding system may be used to determine the probe attached to a selected bead. See, U.S. Pat. Nos. 6,451,536, 6,646,243, 6,544,739, and 6,440,667.

The development of Very Large Scale Immobilized Polymer Synthesis or VLSIPS™ technology has provided methods for making very large arrays of nucleic acid probes in very small arrays. See U.S. Pat. No. 5,143,854 and PCT Patent Publication Nos. WO 90/15070 and WO 92/10092, and Fodor et al., Science, 251, 767-77 (1991), each of which is incorporated herein by reference. U.S. Pat. No. 5,800,992, describes methods for making arrays of nucleic acid probes that can be used to detect the presence of a nucleic acid containing a specific nucleotide sequence. Methods of forming high density arrays of nucleic acids, peptides and other polymer sequences with a minimal number of synthetic steps are known. The nucleic acid array can be synthesized on a solid substrate by a variety of methods, including, but not limited to, light-directed chemical coupling, and mechanically directed coupling.

In a preferred detection method, the array of immobilized nucleic acids, or probes, is contacted with a sample containing target nucleic acids, to which a detectable label is attached. Target nucleic acids hybridize to the probes on the array and any non-hybridized nucleic acids are removed. If the label is fluorescent, the array containing the hybridized target nucleic acids may be exposed to light which excites the fluorescent label. The resulting fluorescent intensity, or brightness, is detected. Relative brightness is used to determine which probe is the best candidate for the perfect match to the hybridized target nucleic acid because fluorescent intensity (brightness) corresponds to binding affinity.

In the array of the present invention the probes are presented in pairs, one probe in each pair being a perfect match to the target sequence and the other probe being identical to the perfect match probe except that the central base is a homo-mismatch. Mismatch probes provide a control for non-specific binding or cross-hybridization to a nucleic acid in the sample other than the target to which the probe is directed. Thus, mismatch probes indicate whether hybridization is or is not specific. For example, if the target is present, the perfect match probes should be consistently brighter than the mismatch probes because fluorescence intensity, or brightness, corresponds to binding affinity. (See, for example U.S. Pat. No. 5,324,633, which is incorporated herein for all purposes.) In addition, if all central mismatches are present, the mismatch probes can be used to detect a mutation. Finally the difference in intensity between the perfect match and the mismatch probe (I(PM)-I(MM)) provides a good measure of the concentration of the hybridized material. See pending PCT Application No. 98/11223, which is incorporated herein by reference for all purposes.

In another embodiment, the current invention provides a pool of sequences which may be used as probes for their complementary targets. A number of uses for nucleic acid probes of defined sequence are known in the art. Some of the uses include: to screen cDNA or genomic DNA libraries, or subclones derived from them, for additional clones containing segments of DNA that have been isolated and previously sequenced; in Southern, northern, or dot-blot hybridization to identify or detect the sequences of specific genes; in Southern, or dot-blot hybridization of genomic DNA to detect specific mutations in genes of known sequence; to detect specific mutations generated by site-directed mutagenesis of cloned genes; as primers for extension by a DNA polymerase, and to map the 5' termini of mRNA molecules by primer extensions. Other uses for probes derived from the sequences disclosed in this invention will be readily apparent to those of skill in the art. See, for example, Lodish et al. *Molecular Cell Biology*, $3^{rd}$ edition, Scientific American Books (1995) p. 229-233, incorporated above, for a description of the construction of genomic libraries.

In another embodiment, the disclosed arrays may be combined with known methods to monitor expression levels of genes in a wide variety of contexts. For example, where the effects of a drug on gene expression are to be determined, the drug will be administered to a culture, sample, or a cell and the gene expression levels will be analyzed. For example, nucleic acids are isolated from the treated culture, sample, cell, or a biological sample from the organism and from an untreated organism sample or cell, hybridized to a high density probe array containing probes directed to the genes of interest and expression levels are determined. Expression levels may be measured relative to the expression of other genes in the sample, for example, genes that are constitutively expressed may be used as normalization controls. The types of drugs that may be used in these types of experiments include, but are not limited to, antibiotics, antivirals, narcotics, anti-cancer drugs, tumor suppressing drugs, and any chemical composition which may affect the expression of genes in vivo or in vitro. Varying growth conditions may also be analyzed for variation in expression.

The current invention is particularly suited to be used in the types of analyses described by, for example, pending U.S. Pat. No. 6,309,822 and PCT Application No. 98/11223, each of which is incorporated by reference in its entirety for all purposes. As described in Wodicka et al., Nature Biotechnology 15 (1997), hereby incorporated by reference in its entirety for all purposes, because mRNA hybridization correlates to gene expression level, hybridization patterns can be compared to determine differential gene expression. As non-limiting examples: hybridization patterns from samples treated with certain types of drugs may be compared to hybridization patterns from samples which have not been treated or which have been treated with a different drug; hybridization patterns for samples infected with a specific virus may be compared against hybridization patterns from non-infected samples; hybridization patterns for samples with cancer may be compared against hybridization patterns for samples without cancer; hybridization patterns of samples from cancerous cells which have been treated with a tumor suppressing drug may be compared against untreated cancerous cells, etc. Zhang et al., Science 276 1268-1272, hereby incorporated by reference in its entirety for all purposes, provides an example of how gene expression data can provide a great deal of insight into cancer research. One skilled in the art will appreciate that a wide range of applications will be available using 2 or more, 10 or more, 100 or more, 1000 or more, 10,000 or more or 100,000 or more of the SEQ ID Nos. 1-120,855 sequences as probes for gene expression analysis.

The combination of the nucleic array technology and the Yeast specific probes in this disclosure is a powerful tool for studying gene expression. Yeast arrays have been used by researchers in a variety of studies.

In another embodiment, the invention may be used in conjunction with the techniques which link specific proteins to the mRNA which encodes the protein. (See for example Roberts and Szostak Proc. Natl, Acad. Sci. 94 12297-12302 (1997). Hybridization of these mRNA-protein fusion compounds to arrays comprised of 2 or more, 10 or more, 100 or more, 1000 or more, 10,000 or more, or 100,000 or more the sequences disclosed in the present invention provides a powerful tool for monitoring expression levels.

In one embodiment, the current invention provides a pool of unique nucleic acid sequences which can be used for parallel analysis of gene expression under selective conditions. Without wishing to be limited, genetic selection under selective conditions could include: variation in the temperature; pH levels; aeration, food (type, texture, amount etc.), carbon source, presence or absence of drugs, inclusion of varying amounts of amino acids; variation in an organism's surroundings; etc. Arrays, such as those in the present invention, can be used to determine whether gene expression is altered when an organism is exposed to selective conditions.

Methods for using nucleic acid arrays to analyze genetic selections under selective conditions are known. (See for example, R. Cho et al., Proc. Natl. Acad. Sci. 95 3752-3757 (1998), incorporated herein in its entirety for all purposes.) Cho et al. describes the use of a high-density array containing oligonucleotides complementary to every gene in the yeast *Saccharomyces cerevisiae* to perform two-hybrid protein-protein interaction screens for *S. cerevisiae* genes implicated in mRNA splicing and microtubule assembly. In another embodiment, the current invention provides a pool of unique nucleic acid sequences which can be used to identify biallelic markers, providing a novel and efficient approach to the study of genetic variation. For example, methods for using high density arrays comprised of probes which are complementary to the genomic DNA of a particular species to interrogate polymorphisms are well known. (See for example, U.S. Pat. No. 6,300,063 which is hereby incorporated by reference herein for all purposes.) Pools of 2 or more, 10 or more, 100 or more, 1000 or more, 10,000 or more, or 100,000 or more of the sequences disclosed in this invention combined with the methods described in the above patent provides a tool for studying genetic variation in the Yeast system.

In another embodiment genetic variation may be correlated with variation in gene expression pattern. Much of the genetic variation between individuals is the result of single nucleotide polymorphisms (SNPs). The presence of SNPs in or near a gene may result in differences in gene expression, which may result, for example, from changes in the rate of transcription, the stability of the mRNA, splicing of the mRNA, or translation of the mRNA. In one embodiment an array comprising SEQ ID Nos. 1-120,855 and probes to genotype selected SNPs in the yeast genome may be used to monitor genotype and expression changes that correlate with differences in genotype.

Arrays of probes to yeast genes have been used to monitor gene expression in a variety of experimental conditions. For example, Evert et al. *J. Biol. Chem.* 279(21), 22585-94, (2004), observed changes in gene expression after spontaneous DNA damage, Gissen et al: *Nat. Genet.* 36(4), 400-4, (2004) observed changes in gene expression after mutation of a specific gene, VPS33B, Jansen et al. *App. Envir. Microbio.* 70(4), 1956-63, (2004) observed changes in gene expression after prolonged grown the maltose-limited media, Kreiman et al. *N.A.R.* 32(9), 2889-900, (2004) identified sets of genes that were co-expressed and identified clusters of cis-regulatory elements in the co-expressed genes, and Orlandi, I. et al. *Jour. of Biol. Chem.* 279(8), 6414-25, (2004) observed changes in expression resulting from a null mutant of ubp10.

In another embodiment of the invention, genetic variation can be used to produce genetic maps of various strains of yeast. Winzeler et al., "Direct Allelic Variation Scanning of the Yeast Genome" *Science*, 281(5380):1194-7. (1998), describes methods for conducting this type of screening with arrays containing probes complementary to the yeast genome. Briefly, genomic DNA from strains which are phenotypically different is isolated, fragmented, and labeled. Each strain is then hybridized to identical arrays comprised of the nucleic acid sequences complementary to the system being studied. Comparison of hybridization patterns between the various strains then serve as genetic markers. As described by Winzler et al, these markers can then be used for linkage analysis. High density arrays created from 2 or more, 10 or more, 100 or more, 1000 or more, 10,000 or more, or 100,000 or more of the sequences disclosed in this invention can be used to study genetic variation using the methods described by Winzler et al.

In another embodiment, the present invention may be used for cross-species comparisons. One skilled in the art will appreciate that it is often useful to determine whether a gene present in one species, for example rat, is present in a conserved format in another species, including, without limitation, *Drosophila*, human, chicken, zebrafish, *Escherichia coli*, mouse or yeast. See, for example, Andersson et al., Mamm. Genome 7(10):717-734 (1996), which is hereby incorporated by reference for all purposes, which describes the utility of cross-species comparisons. The use of 2 or more, 10 or more, 100 or more, 1000 or more, 10,000 or more or 100,000 or more of the sequences disclosed in this invention in an array can be used to determine whether any of the sequence from one or more of the yeast genes represented by the sequences disclosed in this invention is conserved in another species by, for example, hybridizing genomic nucleic acid samples from another species to an array comprised of the sequences disclosed in this invention. Areas of hybridization will yield genomic regions where the nucleotide sequence is highly conserved between the interrogation species and yeast.

In another embodiment, the present invention may be used to characterize the genotype of knockouts. Methods for using gene knockouts to identify a gene are well known. See for example, Lodish et al. *Molecular Cell Biology*, 3$^{rd}$ *Edition*, Scientific American Books pub pp. 292-296 and U.S. Pat. No. 5,679,523, which are hereby incorporated by reference for all purposes. By isolating genomic nucleic acid samples from knockout species with a known phenotype and hybridizing the samples to an array comprised of 2 or more, 10 or more, 100 or more, 1000 or more, 10,000 or more, or 100,000 or more of the sequences disclosed in this invention, candidates genes which contribute to the phenotype will be identified and made accessible for further characterization.

In another embodiment, the present invention may be used to identify new gene family members. Methods of screening libraries with probes are well known. (See, for example, Maniatis et al, incorporated by reference above.) Because the present invention is comprised of nucleic acid sequences from specific known genes, 2 or more, 10 or more, 100 or more, 1000 or more, 10,000 or more, or 100,000 or more of sequences disclosed in this invention may be used as probes to screen genomic libraries to look for additional family members of those genes from which the target sequences are derived.

In another embodiment of the invention, the sequences of this invention may be used to generate primers directed to their corresponding genes as disclosed in the Genbank or any other public database. These primers may be used in such basic techniques as sequencing or PCR, see for example Maniatis et al., incorporated by reference above.

In another embodiment, the invention provides a pool of nucleic acid sequences to be used as ligands for specific genes. The sequences disclosed in this invention may be used as ligands to their corresponding genes as disclosed in the Genbank or any other public database. Compounds which specifically bind known genes are of interest for a variety of uses. One particular clinical use is to act as an antisense protein which specifically binds and disables a gene which has been, for example, linked to a disease. Methods and uses for ligands to specific genes are known. See for example, U.S. Pat. No. 5,723,594, which is hereby incorporated by reference in its entirety for all purposes.

In a preferred embodiment, the hybridized nucleic acids are detected by detecting one or more labels attached to the sample nucleic acids. The labels may be incorporated by any of a number of means well known to those of skill in the art. In one embodiment, the label is simultaneously incorporated during the amplification step in the preparation of the sample nucleic acids. Thus, for example, polymerase chain reaction (PCR) with labeled primers or labeled nucleotides will provide a labeled amplification product. In another embodiment, transcription amplification, as described above, using a labeled nucleotide (e.g. fluorescein-labeled UTP and/or CTP) incorporates a label into the transcribed nucleic acids. Quantum dots and chemiluminescent labels may also be used.

Alternatively, a label may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), phosphorescent labels, enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241, each of which is hereby incorporated by reference in its entirety for all purposes.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label.

The label may be added to the target nucleic acid(s) prior to, or after the hybridization. So called "direct labels" are detectable labels that are directly attached to or incorporated into the target nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an aviden-conjugated fluorophore will bind the biotin bearing hybrid duplexes providing a label that is easily detected. For a detailed review of methods of labeling nucleic acids and detecting labeled hybridized nucleic acids see *Laboratory Techniques in Biochemistry and Molecular Biology*, Vol. 24: *Hybridization With Nucleic Acid Probes*, P. Tijssen, ed. Elsevier, N.Y., (1993), which is hereby incorporated by reference in its entirety for all purposes.

Protocols for target amplification, labeling and preparation, protocols for target hybridization, washing and scanning, data analysis methods and detailed information about useful controls and methods for array analysis are provided, for example, in the Affymetrix GeneChip® Expression Analysis Technical Manual, Revision 4, released in 2004 is available from Affymetrix, Inc. (PN 701045). This manual is hereby incorporated herein by reference for all purposes.

CONCLUSION

The inventions herein provide a pool of unique nucleic acid sequences which are complementary to a plurality of yeast genes. These sequences can be used for a variety of types of analyses. In preferred embodiments the sequences are assembled into an array of probes.

The above description is illustrative and not restrictive. Many variations of the invention will become apparent to those of skill in the art upon review of this disclosure. The scope of the invention should, therefore, be determined not with reference to the above description, but instead be determined with reference to the appended claims along with their full scope of equivalents.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07312035B2). An electronic copy of the "Sequence Listing" will also be available from the USPTO upon request and payment of the fee set forth in 37 CFR 1.19(b)(3).

What is claimed is:

1. An array comprising a plurality of nucleic acid probes, wherein the plurality comprises each of the sequences listed in SEQ ID Nos. 1-120,855, and wherein each probe in the plurality of nucleic acid probes consists of one of the sequences listed in SEQ ID Nos. 1-120,855.

2. The array of claim 1 further comprising at least one probe that is the perfect complement of one of the sequences listed in SEQ ID Nos. 1-120,855.

3. The array of claim 1 wherein said plurality of nucleic acid probes is attached to a solid support.

4. The array of claim 1 wherein each probe is attached to the array in a different localized area that is determinable.

5. The array of claim 1 wherein the array comprises a plurality of beads wherein the probes are attached to the beads and the probes on a bead consist of one of the sequences listed in SEQ ID NO: 1-120,855.

6. The array of claim 1 wherein the array consists of a single contiguous solid support.

7. A method of monitoring gene expression in a biological sample comprising yeast nucleic acid, comprising:
    isolating nucleic acid derived from the sample;
    labeling the nucleic acid;
    hybridizing the labeled nucleic acid to an array comprising a plurality of nucleic acid probes, wherein the plurality comprises each of the sequences listed in SEQ ID Nos. 1-120,855, and wherein each probe in the plurality of nucleic acid probes consists of one of the sequences listed in SEQ ID Nos. 1-120,855; and,
    detecting a hybridization pattern, wherein the intensity of signal resulting from hybridization to probes on the array is used to monitor gene expression levels.

8. The method of claim 7 wherein said monitoring gene expression levels comprises comparing gene expression levels of nucleic acids derived from two or more different samples and further comprises the step of:
    comparing said hybridization patterns between said nucleic acids derived from said two or more different samples.

9. The method of claim 7 wherein the labeled nucleic acid hybridized to the array consists essentially of DNA.

10. The method of claim 7 wherein the yeast is selected from the group consisting of *Saccharomyces cerevisisae* and *Schizosaccharomyces pombe*.

11. The method of claim 7 wherein the labeled nucleic acid hybridized to the array consists essentially of RNA that is in the sense orientation relative to the target mRNA.

12. The method of claim 7 wherein the labeled nucleic acid is hybridized to the array in a single reaction.

13. A method of monitoring gene expression in a yeast sample, comprising:
    isolating nucleic acid derived from the yeast sample;
    labeling the nucleic acid with a detectable label;
    hybridizing the labeled nucleic acid to an array comprising a plurality of nucleic acid probes, wherein the plurality comprises each of the sequences listed in SEQ ID Nos. 1-120,855, and wherein each probe in the plurality of nucleic acid probes consists of one of the sequences listed in SEQ ID Nos. 1-120,855;
    detecting a hybridization pattern; and
    analyzing the hybridization pattern to determine a relative expression level of at least 100 genes.

14. The method of claim 13 wherein the yeast sample is from *Saccharomyces cerevisisae*.

15. The method of claim 13 wherein the yeast sample is from *Schizosaccharomyces pombe*.

* * * * *